United States Patent
Milstein

(10) Patent No.: US 6,906,030 B2
(45) Date of Patent: *Jun. 14, 2005

(54) CARBON-SUBSTITUTED DIKETOPIPERAZINE DELIVERY SYSTEMS

(75) Inventor: Sam J. Milstein, Larchmont, NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/443,713

(22) Filed: May 21, 2003

(65) Prior Publication Data

US 2003/0198658 A1 Oct. 23, 2003

Related U.S. Application Data

(63) Continuation of application No. 10/125,836, filed on Apr. 19, 2002, now Pat. No. 6,663,898, which is a continuation of application No. 09/929,530, filed on Aug. 13, 2001, now Pat. No. 6,395,774, which is a continuation of application No. 08/316,404, filed on Sep. 30, 1994, now Pat. No. 6,331,318.

(51) Int. Cl.$^7$ ..................... A61K 38/28; A61K 38/21; A61K 31/33; A61K 9/14; A61K 45/00
(52) U.S. Cl. .................. 514/3; 514/2; 514/183; 424/85.2; 424/85.4; 424/489
(58) Field of Search ................. 514/490, 493, 514/2, 3, 183, 255.02; 424/489, 85.2, 85.4

(56) References Cited

U.S. PATENT DOCUMENTS

| | | | |
|---|---|---|---|
| 3,976,773 A | 8/1976 | Curran et al. | |
| 4,289,759 A | 9/1981 | Heavener | |
| 4,613,500 A | 9/1986 | Suzuki | |
| 4,757,066 A | 7/1988 | Shiokari et al. | |
| 4,835,312 A | 5/1989 | Itoh et al. | |
| 4,873,087 A | 10/1989 | Morishita et al. | |
| 4,900,730 A | 2/1990 | Miyauchi | |
| 4,925,673 A | 5/1990 | Steiner | |
| 4,927,928 A | 5/1990 | Shroot et al. | |
| 4,983,402 A | 1/1991 | Steiner et al. | |
| 5,244,653 A | 9/1993 | Berke et al. | |
| 5,352,461 A | 10/1994 | Feldstein et al. | |
| 5,401,516 A | 3/1995 | Milstein et al. | |
| 5,443,841 A | 8/1995 | Milstein et al. | |
| 5,447,728 A | 9/1995 | Milstein et al. | |
| 5,451,410 A | 9/1995 | Milstein et al. | |
| 5,541,155 A | * 7/1996 | Leone-Bay et al. | 514/2 |
| 5,578,323 A | * 11/1996 | Milstein et al. | 424/499 |
| 5,601,846 A | * 2/1997 | Milstein et al. | 424/499 |
| 5,629,020 A | * 5/1997 | Leone-Bay et al. | 424/489 |
| 5,643,957 A | * 7/1997 | Leone-Bay et al. | 514/563 |
| 5,693,338 A | * 12/1997 | Milstein | 424/451 |
| 5,714,167 A | * 2/1998 | Milstein et al. | 424/490 |
| 5,766,633 A | * 6/1998 | Milstein et al. | 424/489 |
| RE35,862 E | 7/1998 | Steiner et al. | |
| 5,792,451 A | * 8/1998 | Sarubbi et al. | 424/85.4 |
| 5,811,127 A | * 9/1998 | Milstein et al. | 424/499 |
| 5,824,345 A | * 10/1998 | Milstein | 424/489 |
| 5,840,340 A | * 11/1998 | Milstein et al. | 424/499 |
| 6,331,318 B1 | * 12/2001 | Milstein | 424/490 |
| 6,663,898 B2 | * 12/2003 | Milstein | 424/490 |

FOREIGN PATENT DOCUMENTS

GB  2095994  10/1982

OTHER PUBLICATIONS

International Search Report for PCT/US95/12887 (1996).
Gyore et al. Thermal Analysis, vol 2—Proceeding Fourth ICTA Budapest(1974) 387–394.
Chemical Abstracts, vol. No. 114(22), Abstract No. 214519x (1990).
Gurrieri and Siracusa: "Thermal Condensation of Some alpha–aminoacids with Phatalic Acid" Thermochimica Acta, 7 (1973) 231–239.

* cited by examiner

Primary Examiner—Raymond J. Henley, III
(74) Attorney, Agent, or Firm—Darby & Darby

(57) ABSTRACT

Compositions useful in the delivery of active agents are provided. These delivery compositions include (a) an active agent; and (b) a carrier of at least one mono-C-substituted or di-C-substituted diketopiperazine. Methods for preparing these compositions and administering these compositions are also provided.

23 Claims, 2 Drawing Sheets

CARBON-SUBSTITUTED DIKETOPIPERAZINE DELIVERY SYSTEMS

This is a continuation of application Ser. No. 10/125,836, filed Apr. 19, 2002, now U.S. Pat. No. 6,663,898, which is a continuation of application Ser. No. 09/929,530, filed Aug. 13, 2001, now U.S. Pat. No. 6,395,774, which is a continuation of application Ser. No. 08/316,404, filed Sep. 30, 1994, now U.S. Pat. No. 6,331,318. Each of these prior applications is hereby incorporated herein by reference, in its entirety.

FIELD OF THE INVENTION

The present invention relates to compositions for delivering active agents, and particularly biologically active agents. The carriers in these compositions facilitate the delivery of a cargo to a target. These delivery compositions are particularly useful in the oral delivery of biologically active agents such as pharmacologically or therapeutically active agents. Methods for the preparation and for the administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, or the target itself.

Biologically active agents are particularly vulnerable to such barriers. For example in the delivery to animals of pharmacological and therapeutic agents, barriers are imposed by the body. Examples of physical barriers are the skin and various organ membranes that must be traversed before reaching a target. Chemical barriers include, but are not limited to, pH variations, lipid bi-layers, and degrading enzymes.

These barriers are of particular significance in the design of oral delivery systems. Oral delivery of many biologically active agents would be the route of choice for administration to animals if not for biological, chemical, and physical barriers such as varying pH in the gastrointestinal (GI) tract, powerful digestive enzymes, and active agent impermeable gastrointestinal membranes. Among the numerous agents which are not typically amenable to oral administration are biologically active peptides, such as calcitonin and insulin; polysaccharides, and in particular mucopolysaccharides including, but not limited to, heparin; heparinoids; antibiotics; and other organic substances. These agents are rapidly rendered ineffective or are destroyed in the gastrointestinal tract by acid hydrolysis, enzymes, or the like.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation.

Liposomes have also been described as drug delivery systems for insulin and heparin. See, for example, U.S. Pat. No. 4,239,754; Patel et al. (1976), *FEBS Letters*, Vol. 62, pg. 60; and Hashimoto et al. (1979), *Endocrinology Japan*, Vol. 26, pg. 337.

However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents.

There is still a need in the art for simple, inexpensive delivery systems which are easily prepared and which can delivery a broad range of active agents.

SUMMARY OF THE INVENTION

Compositions useful in the delivery of active agents are provided. These delivery compositions comprise (a) an active agent; and (b) a carrier comprising at least one mono-C-substituted or di-C-substituted diketopiperazine. Biologically active agents and pharmacologically active agents may be incorporated as the active agent, and these compositions may be in the form of microspheres.

Also contemplated is a method for preparing these compositions wherein at least one active agent is mixed with a carrier as described above or wherein the carrier is solubilized in a solvent, and the carrier solution is contacted with the active agent and a precipitator solution in which the carrier is insoluble.

In a further embodiment, the compositions are administered, preferably orally, to animals.

DETAILED DESCRIPTION OF THE INVENTION

Figure 1A:
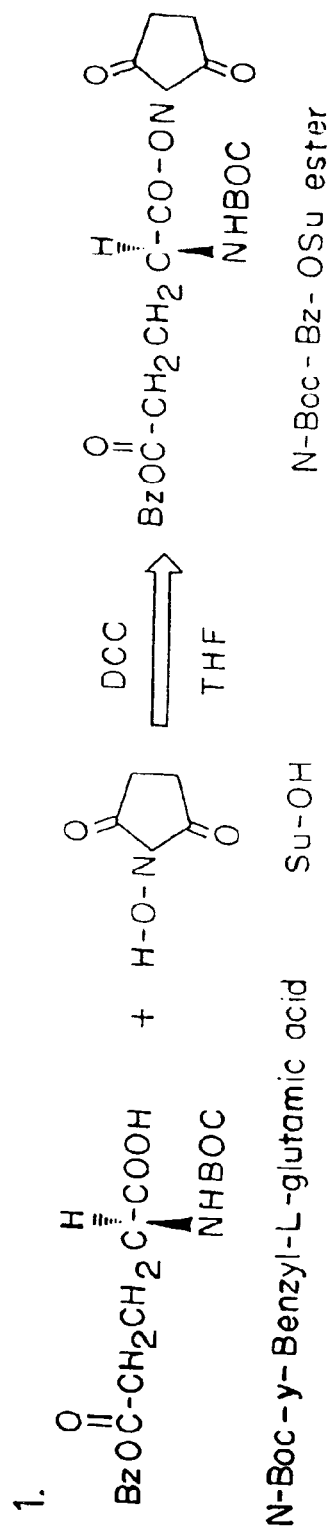
FIGS. 1A and 1B are illustrations of a reaction scheme for the preparation of diketopiperazines.

The present invention is suited to the delivery of any active agents through various biological, chemical, and physical barriers. It is particularly suited to the delivery of active agents which are subject to environmental degradation. Other advantages provided by the present invention include the use of readily available or easy to prepare, inexpensive starting materials. The formulation methods of the present invention are cost-effective for preparing and isolating these compositions, are simple to perform, and are amenable to industrial scale up for commercial production.

Active Agents

Active agents suitable for use in the present invention include biologically active agents, chemically active agents, including, but not limited to, fragrances, as well as other active agents such as, for example, cosmetics.

Biologically active agents include, but are not limited to, pesticides, pharmacological agents, and therapeutic agents. For example, biologically active agents suitable for use in the present invention include, but are not limited to, peptides, and particularly small peptides; hormones, and particularly hormones which by themselves do not or only pass slowly through the gastro-intestinal mucosa and/or are susceptible to chemical cleavage by acids and enzymes in the gastro-intestinal tract; polysaccharides, and particularly mixtures of muco-polysaccharides; carbohydrates; lipids; or any combination thereof. Further examples include, but are not limited to, human growth hormones; bovine growth hormones; growth releasing hormones; interferons; interleukin-1; insulin; heparin, and particularly low molecular weight heparin; calcitonin; erythropoietin; atrial naturetic factor; antigens; monoclonal antibodies; somatostatin; adrenocorticotropin, gonadotropin releasing hormone; oxytocin; vasopressin; cromolyn sodium (sodium or disodium chromoglycate); vancomycin; desferrioxamine (DFO); anti-microbials, including, but not limited to anti-fungal agents; or any combination thereof.

The compositions of the present invention may include one or more active agents.

Diketopinerazines

The diketopiperazines of the present invention are six member ring compounds. The ring includes two nitrogen atoms and is substituted at two carbons with two oxygen atoms. Preferably, the carbonyl groups are at the 1 and 4 ring positions. These rings are further substituted at either or both of the other two carbon atoms of the ring.

Most preferred diketopiperazines are compounds of the formula:

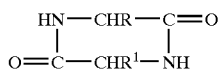    I wherein R and $R^1$ independently are hydrogen, $C_1$–$C_{24}$ alkyl, $C_1$–$C_{24}$ alkenyl, phenyl, naphthyl, ($C_1$–$C_{10}$alkyl) phenyl, ($C_1$–$C_{10}$alkenyl)phenyl, ($C_1$–$C_{10}$ alkyl)naphthyl, ($C_1$–$C_{10}$ alkenyl)naphthyl, phenyl ($C_1$–$C_{10}$ alkyl), phenyl ($C_1$–$C_{10}$ alkenyl), naphthyl ($C_1$–$C_{10}$ alkyl), and naphthyl ($C_1$–$C_{10}$ alkenyl); but both R and $R^1$ can not be hydrogen; either or both R or $R^1$ independently may optionally be substituted with $C_1$–$C_4$ alkyl, $C_1$–$C_4$ alkenyl, $C_1$–$C_4$ alkoxy, —OH, —SH, and —$CO_2R^2$ or any combination thereof; $R^2$ is hydrogen, $C_1$–$C_4$ alkyl or $C_1$–$C_4$ alkenyl; and either or both R and $R^1$ independently may optionally be interrupted by oxygen, nitrogen, sulfur, or any combination thereof.

The phenyl or naphthyl groups may optionally be substituted. Suitable, but non-limiting, examples of substituents are $C_1$–$C_6$ alkyl, $C_1$–$C_6$ alkenyl, $C_1$–$C_6$ alkoxy, —OH, —SH, or $CO_2R^3$ wherein $R^3$ is hydrogen, $C_1$–$C_6$ alkyl, or $C_1$–$C_6$ alkenyl. When one of R or $R^1$ is hydrogen, the diketopiperazine is mono-carbon-(C)-substituted. When neither R nor $R^1$ is hydrogen, the diketopiperazine is di-carbon-(C)-substituted.

Preferably, R, $R^1$, or both R and $R^1$, contain at least one functional group, a functional group being a non-hydrocarbon portion responsible for characteristic reactions of the molecule. Simple functional groups are heteroatoms including, but not limited to halogens, oxygen, sulfur, nitrogen, and the like, attached to, the carbon of an alkyl group by a single or multiple bond. Other functional groups include, but are not limited to, for example, hydroxyl groups, carboxyl groups, amide groups, amine groups, substituted amine groups, and the like.

Preferred diketopiperazines are those which are substituted at one or two of the carbons of the ring with a functional group that includes at least one carboxyl functionality.

Diketopiperazines typically are formed from α-amino acids. The "term" amino acid used with respect to diketopiperazines also includes any carboxylic acid having at least one free α-amine group and includes naturally occurring and synthetic α-amino acids and all optical isomers thereof. Preferably, the diketopiperazines are formed from two amino acids which are the same or optical isomers of one another. Typical amino acids useful in the preparation of diketopiperazines are natural or synthetic amino acids having the formula:

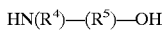    II $R^4$ is hydrogen, $C_1$ to $C_{24}$ alkyl, $C_1$–$C_{24}$ alkenyl, phenyl, naphthyl, ($C_1$–$C_{10}$ alkyl) phenyl, ($C_1$–$C_{10}$ alkenyl) phenyl, ($C_1$–$C_{10}$ alkyl) naphthyl, ($C_1$–$C_{10}$ alkenyl) naphthyl, phenyl ($C_1$–$C_{10}$ alkyl), phenyl ($C_1$–$C_{10}$ alkenyl), naphthyl ($C_1$–$C_{10}$ alkyl), and naphthyl ($C_1$–$C_{10}$ alkenyl); optionally $R^4$ may be substituted with $C_1$–$C_4$ alkyl, $C_1$–$C_4$ alkenyl, $C_1$–$C_4$ alkoxy, —OH, —SH, —$CO_2R^6$, or any combination thereof; $R^6$ is hydrogen $C_1$–$C_4$ alkyl, or $C_1$–$C_4$ alkenyl; and $R^4$ may optionally be interrupted by oxygen, nitrogen, sulfur, or any combination thereof.

The phenyl or naphthyl groups may optionally be substituted. Suitable, but non-limiting examples of substituents are $C_1$–$C_6$ alkoxy, —OH, —SH, or $CO_2R^7$, wherein $R^7$ is hydrogen $C_1$–$C_6$ alkyl, or $C_1$–$C_6$ alkenyl.

$R^5$ has the formula

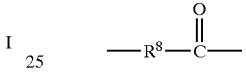

wherein $R^8$ is $C_1$ to $C_{24}$ alkyl, $C_1$ to $C_{24}$ alkenyl, phenyl, naphthyl, ($C_1$ to $C_{10}$ alkyl)-phenyl, ($C_1$ to $C_{10}$ alkenyl) phenyl, ($C_1$ to $C_{10}$ alkyl)naphthyl, ($C_1$ to $C_{10}$ alkenyl) naphthyl, phenyl ($C_1$ to $C_{10}$ alkyl), phenyl ($C_1$ to $C_{10}$ alkenyl), naphthyl ($C_1$–$C_{10}$ alkyl), and naphthyl ($C_1$–$C_{10}$ alkenyl); $R^8$ may optionally be substituted with $C_1$ to $C_{24}$ alkyl or $C_1$ to $C_{24}$ alkenyl; and $R^5$ may optionally be interrupted by oxygen, nitrogen, sulfur or any combination thereof.

The phenyl or naphthyl groups may optionally be substituted. Suitable but non-limiting examples of substituents are $C_1$ to $C_6$ alkyl, $C_1$ to $C_6$ alkenyl, $C_1$–$C_6$ alkoxy, hydroxy, thio, or $CO_2R^9$ alkenyl, wherein $R^9$ is hydrogen, $C_1$–$C_6$ alkyl, or $C_1$–$C_6$ alkenyl.

The preferred naturally occurring amino acids for preparation of the diketopiperazines of the present invention are alanine, arginine, asparagine, aspartic acid, citrulline, cysteine, cystine, glutamine, glycine, histidine, isoleucine, leucine, lysine, methionine, ornithine, phenylalanine, proline, serine, threonine, tryptophan, tyrosine, valine, or hydroxy proline.

The preferred non-naturally occurring amino acids for use herein are phenylglycine, α-aminobutyric acid, α-amino isobutyric acid, aminobenzoic acid, aminohippuric acid, and cysteine.

Preferably, the α-amino acids of which the diketopiperazines are derived are glutamic acid, aspartic acid, tyrosine, phenylalanine, and optical isomers of any of the foregoing. Most preferably, the diketopiperazines useful in the present invention are prepared from trifunctional amino acids such as L-glutamic acid and L-aspartic acid which cyclize to form diketopiperazines.

Dipiperazine ring systems may be generated during thermal polymerization or condensation of amino acids or amino acid derivatives. (Gyore, J; Ecet M. *Proceedings Fourth ICTA (Thermal Analysis)*, 1974, 2, 387–394 (1974)). These six membered ring systems were presumably generated by intra-molecular cyclization of the dimer prior to further chain growth or directly from a linear peptide (Reddy, A. V., *Int. J. Peptide Protein Res.*, 40, 472–476 (1992); Mazurov, A. A. et al., *Int. J. Peptide Protein Res.*, 42, 14–19 (1993)).

Diketopiperazines can also be formed by cyclodimerization of amino acid ester derivatives as described by Katchalski et al., *J. Amer. Chem. Soc.*, 68, 879–880 (1946), by cyclization of dipeptide ester derivatives, or by thermal dehydration of amino acid derivatives and high boiling solvents as described by Kopple et al., *J. Org. Chem.*, 33 (2), 862–864 (1968).

Figure 1A:
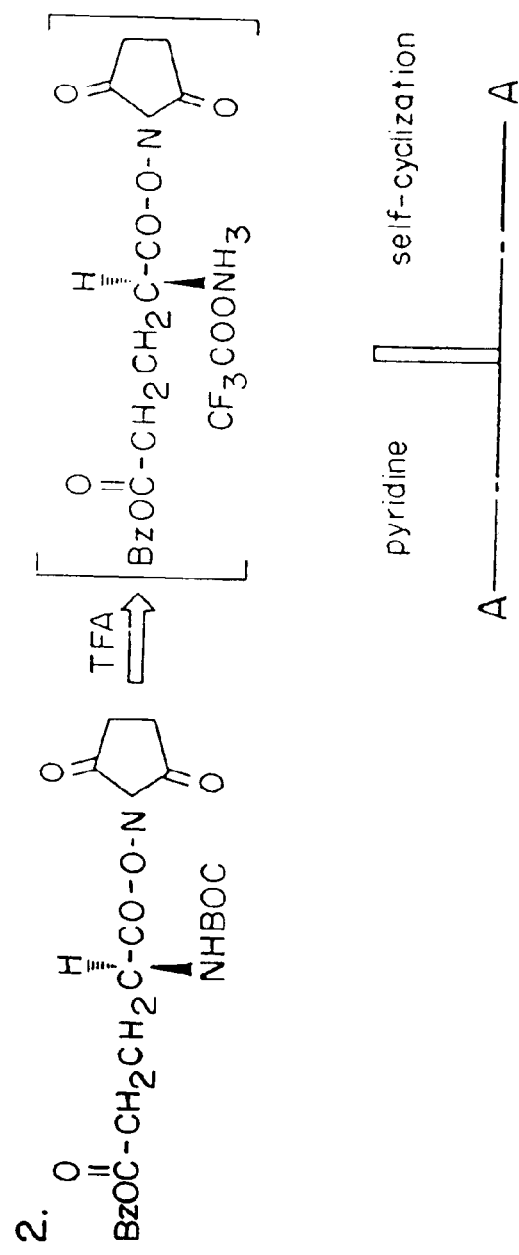
Figure 1B:
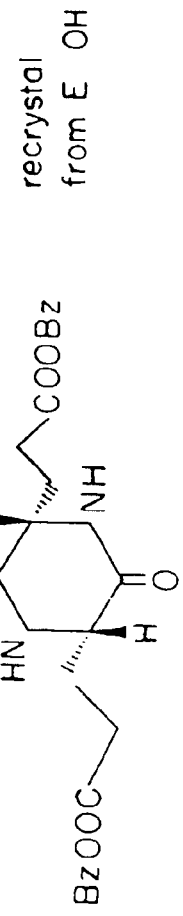
Figure 1B:
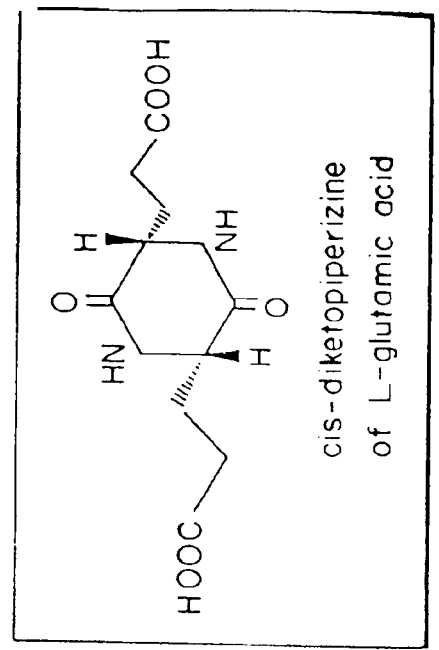
Figure 1B:
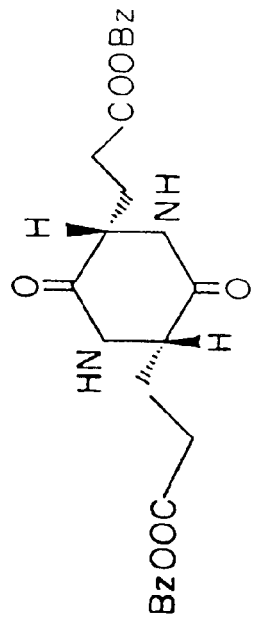

A typical synthesis of a diketopiperazine is illustrated in FIG. 1 The COOH group(s) of an amino acid benzyl ester are activated in step 1 to yield a protected ester. The amine is deprotected and cyclized via dimerization in step, 2, providing a diketopiperazine di-ester. Finally in step 3, the COOH group(s) are deprotected to provide the diketopiperazine.

Ester derivatives of these diketopiperazine carriers are also useful in the present invention.

Delivery Systems

The carriers of the present invention are pharmacologically harmless, as are the microspheres prepared therefrom. They do not effectively impair the active (i.e. biological, chemical, therapeutical, pharmacological, or the like) agent.

The diketopiperazine carriers of the present invention may be used to prepare compositions for delivering active agent cargoes, and particularly biologically active agent cargoes. Delivery compositions which include the active agent and the carrier may be in the form of mixtures of active agent and carrier or the carrier may form a microsphere which contains the active agent. The carrier described herein facilitates the delivery of the cargo to a target.

Microspheres containing an active agent can generally be of the matrix form or the microcapsule form. The matrix form includes both a hollow matrix sphere in which the carrier forms a matrix shell around a hollow center and the active agent is distributed throughout the matrix and a solid matrix sphere in which the carrier forms a spherical matrix continuum in which the active agent is distributed.

The microcapsule form is one in which the encapsulated active agent either is in solution or is a solid, with the carrier forming a shell around the encapsulated material. The microcapsule form is the form most often taken by the self assembly of the carriers of the present invention.

Delivery compositions may be mixtures which may be formulated simply by mixing the carrier with the active agent prior to administration. If the delivery composition is to be of the microsphere form, carrier microspheres can be prepared by dissolving the carrier in an appropriate solute and then stimulating self assembly by contacting the carrier solution with a precipitator. Solubility of the carrier can be regulated by the selection of the appropriate diketopiperazine.

Furthermore, the diketopiperazines, and therefore, the compositions of the present invention can be pH adapted to be selectively soluble in specific acidic, basic, or neutral pH ranges.

Delivery compositions which are targeted to an acidic environment can be made selectively soluble at acidic pH, such as the pH in the stomach. These compositions are prepared with an acid-soluble carrier. The acid-soluble carrier exists largely in the cation form in at least a portion of the pH range from about 1 to about 6.8. However, above about 6.8 or at selected ranges above pH 6.8, the carrier is largely unprotonated and insoluble in water. Therefore, the carrier could self assemble to microspheres at basic or neutral pH, and the active agent in the delivery composition would not be released until the carrier solubilizes upon encountering an acidic pH.

Delivery compositions which are to be targeted to an alkaline environment can be made selectively soluble at alkaline pH, such as the pH in the distal portion of the intestine. These compositions are prepared with a base-soluble carrier. The base-soluble carrier exists largely in an anionic form in at least a portion of the pH range of from about 7.2 to about 11. However, below and at pH 7.2, the carrier is largely protonated and insoluble in water. Therefore, the carrier could self assemble to microspheres at acidic or neutral pH, and the active agent in the delivery composition would not be released until the carrier solubilizes upon encountering a basic pH.

Delivery compositions which are targeted to a neutral environment can be made selectively soluble at neutral pH. These compositions are prepared with a neutral-soluble carrier. The neutral-soluble carrier exists largely in a neutral form at neutral pH, i,e. from about 6.8 to about 7.2. However, above or below this range, the carrier is insoluble in water. Therefore, the carrier could self assemble to microspheres at acidic or basic pH, and the active agent in the delivery composition would not be released until the carrier solubilizes upon encountering a neutral pH.

In a typical formulation, the final solution can contain from about 10 mg to about 2000 mg of carrier per ml of solution, preferably between about 75 to about 500 mg of carrier per ml of solution, and most preferably from about 75 to about 200 mg per ml. Optionally, the mixture is heated to a temperature between about 20° C. and about 60° C., preferably about 40° C., until the carrier dissolves. Particulates remaining in the solution may be filtered out by conventional means such as gravity filtration over filter paper. The carrier solution usually is maintained at the elevated temperature and is mixed with the active agent and a precipitator, for example, an acid solution such as, for example, aqueous acetic or citric acid at a concentration ranging from about 1N to about 3N for acid insoluble carriers, a basic solution for base insoluble carriers, and a neutralizing solution for neutral insoluble carriers. The active agent can be mixed with the precipitating solution or can be used separately. The resultant mixture is maintained for a period of time sufficient for microsphere formation as observed by light microscopy. Although it is preferred that the precipitating solution is added to the carrier solution, the carrier solution can be added to the precipitating solution as well.

The solutions above may optionally contain additives such as stabilizing additives. The presence of such additives promotes the stability and dispersability of the active agent in solution. The stabilizing additives may be employed at a concentration ranging between about 0.1 and 5% (w/v), preferably about 0.5% (w/v). Suitable, but non-limiting examples of stabilizing additives include buffer salts, gum acacia, gelatin, methyl cellulose, polyethylene glycol, and polylysine. The preferred stabilizing agents are gum acacia, gelatin, and methyl cellulose.

The amount of active agent which may be encapsulated by the microsphere is dependent upon a number of factors which include the concentration of agent in the encapsulating solution as well as the affinity of the agent for the carrier. The concentration of the active agent in the final formulation also will vary depending on the required dosage of treatment. When necessary, the exact concentration can be determined by, for example, reverse phase HPLC analysis.

When the present compositions are in microsphere form, the particle size of the microsphere can also aid in providing efficient delivery of the active agent to the target. Typically, microspheres of the present invention will have a diameter of less than 10 μm, preferably in the range of from about 0.1 μm to about 10 μm, and most preferably in the range of from 0.2 μm to about 10 μm. The size of the microspheres containing an active agent can be controlled by manipulating a variety of physical or chemical parameters, such as the pH, osmolarity, ionic strength of the encapsulating solution, or size of the ions in solution, and/or by the choice of the precipitator used in the microsphere forming and loading process.

For example, in the GI tract it is often desirable to use microspheres which are sufficiently small to deliver effectively the active agent at the targeted area within the gastrointestinal tract. Small microspheres can also be administered parenterally by suspending the spheres in an appropriate carrier fluid (e.g. isotonic solution) and injecting the solution directly into the circulatory system, intramuscularly, or subcutaneously. The mode of administration of the delivery compositions will vary, of course, depending upon the requirement of the active agent administered. It has been noted that large amino acid microspheres (greater than 50 μm) tend to be less effective as oral delivery systems.

The delivery compositions of the present invention may also include one or more enzyme inhibitors. Such enzyme inhibitors include, but are not limited to, compounds such as actinonin or epiactinonin and derivatives thereof. These compounds have the formulas below:

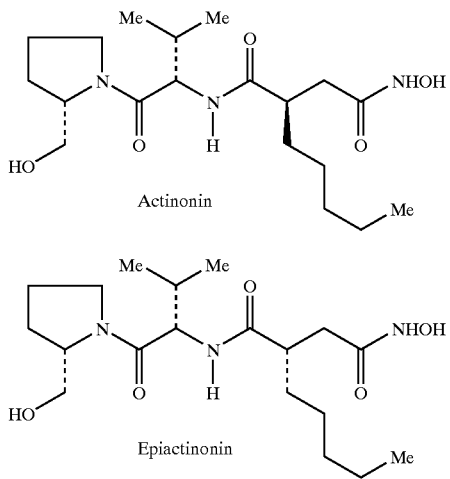

Derivatives of these compounds are disclosed in U.S. Pat. No. 5,206,384. Actinonin derivatives have the formula:

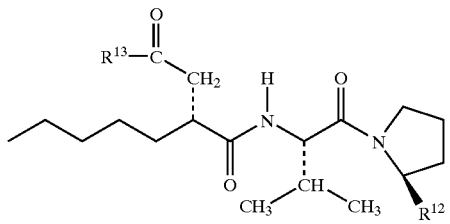

wherein $R^{12}$ is sulfoxymethyl or carboxyl or a substituted carboxy group selected from carboxamide, hydroxyaminocarbonyl and alkoxycarbonyl groups; and $R^{13}$ is hydroxyl, alkoxy, hydroxyamino or sulfoxyamino group. Other enzyme inhibitors include, but are not limited to, aprotinin (Trasylol) and Bowman-Birk inhibitor.

The delivery compositions of the present invention may be formulated into dosage units by the addition of one or more excipient(s), diluent(s), disintegrant(s), lubricant(s), plasticizer(s), colorant(s), or dosing vehicle(s). Preferred dosage unit forms are oral dosage unit forms. Most preferred dosage unit forms include, but not limited to, tablets, capsules, or liquids. The dosage unit forms can include biologically, pharmacologically, or therapeutically effective amounts of the active agent or can include less than such an amount if multiple dosage unit forms are to be used to administer a total dosage of the active agent. Dosage unit forms are prepared by methods conventional in the art.

The compositions of the subject invention are useful for administering biologically active agents to any animals such as birds; mammals, such as primates and particularly humans; and insects. The system is particularly advantageous for delivering chemical or biologically active agents which would otherwise be destroyed or rendered less effective by conditions encountered before the microsphere reaches its target zone (i.e. the area in which the active agent of the delivery composition are to be released) and within the body of the animal to which they are administered. Particularly, the compositions of the present invention are useful in orally administering active agents, especially those which are not ordinarily orally deliverable.

Description of the Preferred Embodiments

The following examples illustrate the invention without limitation.

Reagents were purchased from Sigma Chemical Co.—St. Louis, Mo., and were used without further purification. Flash column chromatography was performed on Silica gel 40 mm, obtained from J. T. Baker—Co. NMR spectra were recorded on Varian EM-390, VXR-300, or QE-300 instruments and were run with chemical shifts given in pats per million downfield from an internal tetramethylsilane or sodium 3-(trimethylsilyl)-propionate standard. Mass spectra were obtained on a Kratos MS 8ORFA or a Finnigan 4516 MS instrument. All optical rotations were performed at 589 nm (the Na D-line) at 22° C. on a Perkin-Elmer 241 polarimeter, with "c" expressed as g of compound per 100 ml of solvent. Melting points are uncorrected.

EXAMPLE 1

Diketopiperazine of L-glutamic Acid

NαBOC-γ-benzyl-L-glutamic acid (NBGA) (6.0 g, 17.8 mmol) and N-hydroxy succinimide (2.25 g, 19.6 mmol) were dissolved in anhydrous tetrahydrofuran (THF) (150 mL). The solution was cooled to 0° C. in an ice bath and dicyclohexylcarbodimide (DCC) (4.04 g, 19.6 mmol) dissolved in 40 mL anhydrous THF was added dropwise over 30 minutes. The ice bath was removed. The solution was allowed to warm to room temperature and was stirred overnight. The reaction was monitored by thin layer chromatography (TLC) (20% EtOH/CHC₃).

When the reaction was completed, the solution was filtered and the filtrate was concentrated to provide crude N-hydroxy succinimide (NHS) ester of NαBOC-γbenzyl-L-glutamic acid as a viscous semi-solid (8.7 g).

Trifluoroacetic acid (TFA, 1.3 mL) was added dropwise to a portion of this NHS ester (0.50 g, 1.02 mmol) at 0° C. The solution was slowly allowed to warm to room temperature and was stirred overnight.

The volatile material was removed at reduced pressure, and a crude yellow solid (0.85 g) was recrystallized from EtOAc to provide pure diketopiperazine L-glutamic acid dibenzyl ester (0.11 g, 50%).

Properties of the diketopiperazine are listed below.

m.p. 275–277° C.
$^1$H NMR($d_6$-DMSO): δ8.26(s, 2H, NH), 7.46(s, 10H, aromatic), 5.16(s, 4H, $CH_2$), 3.98(t, 2H, CH), 2.58(m, 4H, CH2), 2.06(m, 4H, CH2).
Analysis: Calc. for $C_{24}H_{26}N_2O_6$: C 66.74, H 5.98, N 6.39:
Found: C 65.73, H 6.03, N 6.35.
Mass spectrum: Theoretical: 438.18;
Found: 439 (M + 1).
Optical rotation: $[\alpha]_D$ -23.4° (c = 1, dioxane).

EXAMPLE 2

Diketopiperazine of L-glutamic Acid

The diketopiperazine of L-glutamic acid dibenzyl ester was prepared according to the method of Example 1 (0.90 g, 2.05 mmol, 4.1 mequiv.) and was dissolved in a mixture of EtOAc/MeOH (6:1, 470 ml). Pd-C (0.20 g) catalyst was added. The black suspension was degassed three times, and hydrogen gas was introduced. The reaction was monitored by TLC (30% EtOH/$CHCl_3$).

The catalyst was filtered off, and the resultant diacid precipitate was washed five times with boiling MeOH and EtOAc to dissolve the diacid. The filtrate was concentrated to provide the diketopiperazine of L-glutamic acid as a white solid (0.53 g, 100%).

Properties of the diketopiperazine are listed below:

m.p. 234–236° C.
$^1$H NMR($d_7$-DMF): δ4.00(t, 2H, CH), 2.49(m, 4H, $CH_2$), 2.10(m, 4H, $CH_2$).
Analysis: Calc. for: $C_{10}H_{14}N_2O_6$: C 46.51; H 5.46; N 10.85:
Found: C 46.72; H 5.50; N 10.82.
High resolution mass spectrum: Theoretical: 259.0930 (M + H);
Found: 259.033 (M + H).
Optical rotation: $[\alpha]_D$ -52° (c = 1, DMSO).

EXAMPLE 3

Diketopiperazine of L-aspartic Acid

The method of Example 1 was followed, substituting β-benzyl-Nα-BOC-L-aspartic acid (24.0 g, 74.2 mmol) for the NBGA, 9.40 g (81.7 mmol) of the NHS, and 16.85 g (81.7 mmol) of the DDC in anhydrous THF to provide 37.13 g of crude NHS ester.

This NHS ester (37.13 g) was reacted with TFA (85 ml) at 0° C. to yield a crude TFA salt. The salt was neutralized in dry dimethylformamide (DMF) (100 mL) and pyridine (3.5 L) at 0° C. Recrystallization from EtOAc provided the diketopiperazine of L-aspartic acid dibenzyl ester as a white solid (7.13 g, 47%) m.p. 157° C.

Properties of the diketopiperazine are listed below.

1H NMR($CDCl_3$) δ7.31(s, 10H, aromatic) 6.72(s, 2H, NH), 5.12(s, 4H, $CH_2$), 4.35(m, 2H, CH), 3.00(m, 4H, $CH_2$).
Analysis: Calc. for $C_{22}H_{22}N_2O_6$: C 64.38; H 5.40; N 6.83:
Found: C 64.27; H 5.39; N 6.79.
High resolution mass spectrum: Theoretical: 410.1478:
Found: 410.1503.
Optical rotation: $[\alpha]_D$ -69.50' (c = 1, $CHCL_3$).

EXAMPLE 4

Diketopiperazine of L-aspartic Acid

The diketopiperazine of L-aspartic acid dibenzyl ester (6.15 g, 15 mmol, 30 mequiv.) was prepared according to the method of Example 3 and was dissolved in MeOH (250 mL). Pd-C (0.90 g) catalyst was added. The black suspension was degassed three times, and hydrogen gas introduced. The reaction was monitored by TLC (30% EtOH/$CHCl_3$).

The catalyst was filtered off, and resultant diacid precipitate was washed five times with boiling MeOH to dissolve the diacid. The filtrate was concentrated to provide a white solid which was rinsed with MeOH and dried to provide the diketopiperazine of L-aspartic acid as a white solid (2.78 g, 80%).

Properties of the diketopiperazine are listed below.

m.p. 254–255° C.
$^1$H NMR($CDCl_3$-$d_6$ DMSO, 1:1 by vol) δ7.80(s, 2H, NH), 4.20(t, 2H, CH), 2.82(D, 4H, $CH_2$).
Analysis: Calc. for $C_8H_{10}N_2O_6$: C 41.75; H 4.38; N 12.17:
Found: C 41.82; H 4.39; N 12.09.
Optical rotation: $[\alpha]_D$ -37° (c = 1, DMSO).

EXAMPLES 5–8

The diketopiperazines prepared according to the methods of Examples 1–4 (0.1 mmol) are dissolved in 0.1 ml of aqueous $Li_2CO_3$ (1M) deionized water to provide a clear solution of the lithium salt. 50 μl of this 1 M solution are mixed with 50 μl of 0.86M citric acid. The mixture is shaken to yield a white suspension. Microspheric examination of the suspension reveals the presence of tiny spheres which move randomly throughout the field of inspection. Spheres ranging in size up to about 10 μl are observed.

EXAMPLES 9–12

Preparation of Diketopiperazine Microspheres Containing Encapsulated Salmon Calcitonin Diketopiperazines prepared according to the methods of Examples 1–4 are dissolved at 40° C. in distilled water (640 μL) with 100 μl of Tris base tris(hydroxymethylamine) in distilled water, to prepare a solution having a carrier concentration of 50 mg/ml. Water is added to bring the total volume to 4.0 ml. The sample has a carrier concentration of 200 mg/mL. Salmon calcitonin (6 μg) and 2M citric acid are added to the solution. The total salmon calcitonin concentration is 1.5 μg/mL. Microspheres containing salmon calcitonin are observed.

EXAMPLES 13–16

In Vivo Evaluation of Calcitonin Preparations in Rats

Six fasted rats are anesthetized. The rats are administered, by oral gavage, diketopiperazine/calcitonin compositions containing 1.5 μg of calcitonin/ml prepared by the methods of Examples 9–12. Each rat is administered a dosage of 10 μg/kg. The amount of diketopiperazine in the dosage is 300 mg/kg.

Blood samples are collected serially from the tail artery. Serum calcium is determined by testing with a Demand™ Calcium Kit (Sigma Chemical Company—St. Louis, Mo.).

Comparative Example 13A

In Vivo Evaluation of Calcitonin Preparations in Rats

A second group of rats is administered, by oral gavage, 10 μg/kg of salmon calcitonin without any carrier.

EXAMPLES 17–20

In Vivo Evaluation of Interferon Preparations in Rats

A dosing preparation is prepared containing interferon α2b and diketopiperazine carriers prepared according to the methods of Examples 1–4 in a Trizma® hydrochloride buffer solution (Tris-HCl) at a pH of about 7–8.

The samples containing the interferon α2b and carrier are administered by oral gavage, to five rats. The dose is 1000 μg/kg. The amount of carrier is 800 mg/kg. Delivery is evaluated by using an ELISA assay (BioScience Int.'l.— Camarillo, Calif.) for human interferon α.

EXAMPLES 21–24

Toxicity Studies

Male mice (BALB/c) are fed a dose of 1 g/kg of the diketopiperazine prepared according to the methods of Examples 1–4 per day for five (5) days. The compound shows neither acute nor chronic toxicity (over the 5 day period), and no unusual behavior is observed.

EXAMPLE 25–28

In vitro Enzyme Kinetics of Pancreatin Digestion of Salmon Calcitonin

The following solutions are prepared:

Salmon calcitonin (sCt), 10 mg/ml in 0.085 N citric acid; potassium phosphate (monobasic), 7 mg/ml (titrated to pH 7 with 1 N NaOH); pancreatin, 20 mg/ml in potassium phosphate solution; diketopiperazine carriers are prepared by dissolving carriers prepared according to the methods of Examples 1–4 in potassium phosphate solution, titrating to pH 7.2±0.1 (1 N NaOH or HCl as needed), heating to 37° C., stirring, and filtering through 0.2μ syringe filter.

Eight 1.7 ml eppendorf tubes are prepared. Two ml of the carrier solution are placed in several 5 ml stoppered tubes. Two ml of potassium phosphate solution are placed in control tubes (5 ml). 100 μl of sCT stock solution are added to each 5 ml tube. The solutions are vortexed, and a 100 μl aliquot of each tube is transferred to the first eppendorf tube in each set (baseline). The eppendorf tubes are immediately cooled to −78° C. in a dry ice/acetone bath and stored for analysis at a later time. 100 μl of pancreatin stock solution are added to each tube. The tubes are vortexed. 100 μl of the solution are transferred to a second eppendorf tube and are frozen. The 5 ml tubes with the reagents are placed in a 37° C. water bath for one hour. Samples are obtained at the following times 0 min. (baseline), 0.1 min., 1 min., 5 min., 10 min., 15 min., 30 min., and 60 min. Samples are kept at −70° C. until ready for assay.

The samples are assayed using HPLC to determine the amount of calcitonin remaining. The conditions are as follows:

| | |
|---|---|
| Column: | RANIN C4 3 cm × 4.6 mm, 10 μm particle size, 300 Å pore size |
| (Solvent) | |
| Mobile Phase A: | 10% CH₃CN/90% H₂O in 20 mM potassium phosphate buffer at pH 7 |
| Mobile Phase B: | 60% CH₃CN/40% H₂O in 20 mM potassium phosphate buffer at pH 7 |
| Pump: | Hitachi L-6200 Intelligent Pump |

| Linear Gradient: | STEP | TIME (min) | A | B |
|---|---|---|---|---|
| | 1 | 0 | 70% | 30% |
| | 2 | 7 | 40% | 60% |
| | 3 | 7.1 | — | 100% |
| | 4 | 80 | — | 100% |
| | 5 | 8.1 | 70% | 30% |
| Flow Rate: | 2.5 ml/min | | | |

Step 1–2 is a linear gradient from 70%A/30%B to 40%A/60%B. Steps 2–3 is a direct charge to 100%B for 0.9 min followed by a direct charge to 70%A/30%B at 8.1 min.

Detector: UV 220 nm

Comparative Example 25A

The procedure of Examples 25–28 is followed omitting the addition of carrier solution to the eppendorf tubes.

All patents, applications, test methods, and publications mentioned herein are hereby incorporated by references.

Many variations of the present invention will suggest themselves to those skilled in the art in light of the above detailed disclosure. All such modifications are within the full intended scope of the appended claims.

What is claimed is:

1. A delivery composition comprising:
   (a) a peptide; and
   (b) at least one diketopiperazine having the formula:

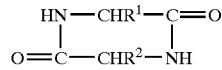

wherein $R^1$ and $R^2$ are $C_1$–$C_{24}$ alkyl or $C_1$–$C_{24}$ alkenyl and have at least one functional group selected from the group consisting of oxygen, amide, and carboxyl groups;
   both $R^1$ and $R^2$, optionally, are substituted with $C_1$–$C_4$ alkyl, $C_1$–$C_4$ alkenyl, $C_1$–$C_4$ alkoxy, —OH, —SH, and —$CO_2R^3$ or any combination thereof; wherein $R^3$ is hydrogen, $C_1$–$C_4$ alkyl, or $C_1$–$C_4$ alkenyl; and
   $R^1$ and $R^2$ are interrupted by oxygen, nitrogen, sulfur, or any combination thereof.

2. A delivery composition as defined in claim 1, comprising a microsphere.

3. A delivery composition as defined in claim 2, wherein said microsphere comprises a microcapsule.

4. A delivery composition as defined in claim 2, wherein said microsphere has a diameter of less than about 10 μm.

5. The delivery composition as defined in claim 1, wherein said peptide is selected from the group consisting of human growth hormone, bovine growth hormone, growth hormone-releasing hormone, an interferon, interleukin-I, interleukin-II, insulin, heparin, calcitonin, erythropoietin, atrial naturetic factor, a monoclonal antibody, somatostatin, adrenocorticotropin, gonadotropin releasing hormone, oxytocin, vasopressin, vancomycin, or any combination of any of the foregoing.

6. A delivery composition as defined in claim 1, wherein said peptide is selected from the group consisting of an interferon, interleukin-I, interleukin-II, insulin, heparin, calcitonin, oxytocin, vasopressin, vancomycin, or any combination of any of the foregoing.

7. A delivery composition as defined in claim 1, wherein said diketopiperazine is derived from two α-amino acids.

8. A delivery composition as defined in claim 7, wherein said two α-amino acids from which said diketopiperazine is derived are the same.

9. A delivery composition as defined in claim 7, wherein said diketopiperazine is prepared by the thermal condensation of said two α-amino acids from which said diketopiperazine is derived.

10. A delivery composition as defined in claim 1, further comprising (c) at least one enzyme inhibitor.

11. A delivery composition as defined in claim 1, wherein $R^1$ and $R^2$ are interrupted by nitrogen.

12. A delivery composition as defined in claim 1, wherein at least one functional group in $R^1$ and $R^2$ is carboxyl.

13. A delivery composition as defined in claim 11, wherein at least one functional group in $R^1$ and $R^2$ is carboxyl.

14. A delivery composition as defined in claim 1, wherein the peptide is insulin.

15. A delivery composition as defined in claim 1, wherein the peptide is calcitonin.

16. A delivery composition as defined in claim 1, wherein the delivery composition is a solution comprising from about 10 to about 2000 mg of the diketopiperazine per ml of solution.

17. The delivery composition of claim 16, wherein the solution comprises from about 75 to about 500 mg of the diketopiperazine per ml of solution.

18. A pharmacological composition comprising:
(a) a peptide; and
(b) at least one diketopiperazine having the formula:

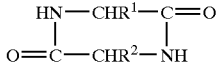

wherein $R^1$ and $R^2$ are $C_1$–$C_{24}$ alkyl or $C_1$–$C_{24}$ alkenyl and have at least one functional group selected from the group consisting of oxygen, amide, and carboxyl groups;

both $R^1$ and $R^2$, optionally, are substituted with $C_1$–$C_4$ alkyl, $C_1$–$C_4$ alkenyl, $C_1$–$C_4$ alkoxy, —OH, —SH, and —$CO_2R^3$ or any combination thereof; wherein $R^3$ is hydrogen, $C_1$–$C_4$ alkyl, or $C_1$–$C_4$ alkenyl;

$R^1$ and $R^2$ are interrupted by oxygen, nitrogen, sulfur, or any combination thereof.

19. A dosage unit form comprising:
(A) a delivery composition as defined in claim 1; and
(B) (a) an excipient,
(b) a diluent,
(c) a disintegrant,
(d) a lubricant,
(e) a plasticizer,
(f) a colorant,
(g) a dosing vehicle, or
(h) any combination thereof.

20. A dosage unit form as defined in claim 19, comprising an oral dosage unit form.

21. A method for administering a peptide to an animal in need thereof, said method comprising administering orally to said animal, a composition as defined in claim 1.

22. A method for preparing microspheres containing an active agent, said method comprising:
(A) forming a diketopiperazines solution by solubilizing, in a solvent, at least one diketopiperazine having the formula:

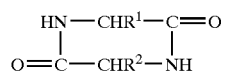

wherein $R^1$ and $R^2$ are $C_1$–$C_{24}$ alkyl or $C_1$–$C_{24}$ alkenyl and have at least one functional group selected from the group consisting of oxygen, amide, and carboxyl groups;

both $R^1$ and $R^2$, optionally, are substituted with $C_1$–$C_4$ alkyl, $C_1$–$C_4$ alkenyl, $C_1$–$C_4$ alkoxy, —OH, —SH, and —$CO_2R^3$ or any combination thereof; wherein $R^3$ is hydrogen, $C_1$–$C_4$ alkyl, or $C_1$–$C_4$ alkenyl;

$R^1$ and $R^2$ are interrupted by oxygen, nitrogen, sulfur, or any combination thereof; and (B) contacting said diketopiperazine solution with a peptide and a precipitator solution in which said diketopiperazine is insoluble.

23. A method as defined in claim 22, wherein said diketopiperazine solution has a pH within a first range and said precipitator solution has a pH within a second range, said first range being different than said second range.

* * * * *